United States Patent [19]

Kuwata et al.

[11] Patent Number: 4,894,224
[45] Date of Patent: Jan. 16, 1990

[54] ORGANOPOLYSILOXANE COMPOSITION

[75] Inventors: Satoshi Kuwata, Annaka; Ikuo Fukui, Joetsu, both of Japan

[73] Assignee: Shin-Etsu Chemical Co., Ltd., Tokyo, Japan

[21] Appl. No.: 183,879

[22] Filed: Apr. 20, 1988

[30] Foreign Application Priority Data

Apr. 20, 1987 [JP] Japan ................... 62-96700

[51] Int. Cl.$^4$ .......................... A61K 7/00; A61K 7/06; A61K 7/48
[52] U.S. Cl. ...................................... 424/78; 514/772; 514/777; 514/778; 514/781; 514/789; 106/171; 106/243
[58] Field of Search .............. 106/171, 170, 244, 243; 514/781, 778, 777, 772, 789; 424/78

[56] References Cited

U.S. PATENT DOCUMENTS 3,940,384  2/1976  Teng et al. ............................ 536/66
4,780,145 10/1988  Mori et al. ....................... 106/208 X

FOREIGN PATENT DOCUMENTS 24478  3/1981  Japan ................................... 514/777
 207313  9/1986  Japan .
2064363  6/1981  United Kingdom ................ 514/772

OTHER PUBLICATIONS

Enclopedia of Polymer Science and Technology, 2nd Ed., vol. 7, pp. 589-613, 1987, John Wiley & Sons.

Primary Examiner—Ellis P. Robinson
Assistant Examiner—Susan Rucker
Attorney, Agent, or Firm—Millen, White & Zelano

[57] ABSTRACT

The organopolysiloxane composition of the invention is a highly viscous liquid or paste suitable as a base of pasty cosmetic and medicinal preparations such as creams, hair-dressings, ointments and the like. The composition comprises an oligomeric cyclic organopolysiloxane compound, an oleaginous material and a cellulose ether esterified with long-chain alkanoyl groups as the thickening agent. The cosmetic and medicinal preparations prepared from the inventive composition as the base have good spreadability on the human skin and are capable of giving very refreshing feeling to the user or patient without lasting stickiness.

9 Claims, No Drawings

ORGANOPOLYSILOXANE COMPOSITION

BACKGROUND OF THE INVENTION

The present invention relates to an organopolysiloxane composition or, more particularly, to a composition having pasty consistency suitable for the base of various cosmetic and medicinal preparations such as cosmetic creams, hair dressings, ointments and the like compounded with a cyclic organopolysiloxane compound having volatilizability as the principal ingredient.

It is well known that a silicone oil or an organopolysiloxane fluid is admixed with a pasty material used as the base of various cosmetic and medicinal preparations such as creams, hair dressings, ointments and the like. The silicone oil in these applications is used merely as an additive in a relatively small amount. Namely, silicone oils are rarely used as a principle ingredient in such a pasty composition. When a silicone oil-based pasty composition is desired, it is usual that the silicone oil is compounded with a considerably large amount of an inorganic filler as a thickening agent such as finely divided silica powder optionally rendered hydrophobic by a surface treatment, bentonite and the like to impart a pasty consistency. The silicone oil compounded with such a thickening agent still should have a relatively high viscosity of, for example, at least 100 centistokes at 25° C. so that the pasty composition prepared from such a viscous silicone oil and a thickening agent is sometimes not acceptable by the users of the cosmetic preparations or the patients using the medicinal preparations because of the heavy spreadability on the human skin in application and lack of refreshingness due to the lasting stickiness as a consequence of the absence of any volatile constituents in the preparations.

Use of a low-viscosity cyclic organopolysiloxane has been proposed in place of the high-viscosity silicone oils in the above mentioned applications (see, for example, Japanese Patent Kokai No. 61-271206, 61-246112 and 62-12710). Since these cyclic organopolysiloxanes have a low viscosity, the composition composed of such a cyclic organopolysiloxane and a thickening agent alone can hardly be imparted with a pasty consistency. Alternatively, a proposal is made to use a silicone resin having three-dimensional siloxane linkages in place of the above mentioned inorganic thickening agents for the cyclic organopolysiloxanes to impart a pasty consistency. This method is also not satisfactory because silicone resins have relatively poor thickening effects for the cyclic organopolysiloxanes unless the compounded amount thereof is quite large with a consequent decrease in the relative content of the cyclic organopolysiloxane so that no smooth and light spreadability of the preparation on the skin and refreshingness can be obtained.

Investigations have of course been undertaken for the use of various thickening agents conventionally used in cosmetic and medicinal preparations including cellulose derivatives such as nitrocellulose, ethyl cellulose and the like and fatty acid esters of polysaccharides. These conventional thickening agents, however, cannot be used for cyclic organopolysiloxanes because they are poorly compatible with organopolysiloxanes not to be dissolved therein though not absolutely without swellability.

SUMMARY OF THE INVENTION

The present invention accordingly has an object to provide an organopolysiloxane composition having a pasty consistency suitable as a base of cosmetic and medicinal preparations without the above described problems and disadvantages in the prior art compositions formulated by using a cyclic organopolysiloxane as the principal ingredient.

Thus, the organopolysiloxane composition of the present invention having a highly viscous or pasty consistency comprises, in admixture:

(A) from 90 to 30% by weight of a cyclic organopolysiloxane represented by the general formula

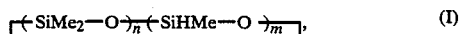

in which Me is a methyl group and m and n are each zero or a positive integer not exceeding 8 with the proviso that m+n is a positive integer of 3 to 8;

(B) from 5 to 50% by weight of an oleaginous material selected from the group consisting of esters of a saturated fatty acid having 8 to 20 carbon atoms in a molecule and a saturated aliphatic alcohol having 1 to 20 carbon atoms in a molecule, animal oils, vegetable oils, squalane and petrolatum; and (C) from 2 to 30% by weight of a cellulose ether having ester-forming substituent groups derived from a saturated fatty acid having 10 to 20 carbon atoms in a molecule, the total amount of the components (A),(B) and (C) being taken as 100% by weight.

In particular, the cyclic organopolysiloxane represented by the general formula (I) given above is preferably decamethyl cyclopentasiloxane or octamethyl cyclotetrasiloxane.

DETAILED DESCRIPTION OF THE PREFERRED EMBODIMENTS

According to the discovery obtained in the investigations undertaken by the inventors, a cyclic organopolysiloxane such as octamethyl cyclotetrasiloxane can be imparted with a pasty consistency when compounded with the above specified components (B) and (C), which are compatible with and dissolved in the cyclic organopolysiloxane when the mixture is heated and agitated at, for example, 70° to 130° C. The uniform mixture can be cooled as such into a relatively clear pasty matter without phase separation. The thus prepared pasty composition can be used as a base of cosmetic creams, hair dressings, ointments and other preparations which exhibit light and smooth spreadability on the human skin and are capable of giving refreshingness to the user without prolongedly reserved feeling of wetness because the cyclic organopolysiloxane has volatilizability to be lost when the preparation is spread over the skin.

The component (A) in the inventive composition is a cyclic organopolysiloxane represented by the above given general formula (I) which shows a cyclotri- to cyclooctasiloxane according to the definitions of the subscripts m and n. Namely, 3 to 8 siloxane units are contained in a molecule which may be any combination of dimethyl siloxane unit (—SiMe$_2$—O—) and methyl hydrogen siloxane unit (—SiHMe—O—). In particular, those cyclic organopolysiloxanes composed of the dimethyl siloxane units (—SiMe$_2$—O—) alone are preferred.

Examples of suitable cyclic organopolysiloxane include hexamethyl cyclotrisiloxane, octamethyl cyclotetrasiloxane, decamethyl cyclopentasiloxane, dodecamethyl cyclohexasiloxane, tetradecamethyl cycloheptasiloxane, hexadecamethyl cyclooctasiloxane, tetramethyl cyclotetrasiloxane, pentamethyl cyclopentasiloxane, pentamethyl cyclotetrasiloxane, hexamethyl cyclotetrasiloxane, heptamethyl cyclotetrasiloxane, hexamethyl cyclopentasiloxane, octamethyl cyclopentasiloxane, heptamethyl cyclopentasiloxane, nonamethyl cyclopentasiloxane and the like. These cyclic organopolysiloxanes can be used either singly or as a combination of two kinds or more according to need. The cyclic organopolysiloxane is preferably decamethyl cyclopentasiloxane or octamethyl cyclotetrasiloxane. The organopolysiloxane composition of the invention contains from 90 to 30% by weight or, preferably, from 85 to 40% by weight of the cyclic organopolysiloxane as the component (A). When the amount of the component (A) is too small, the composition cannot exhibit light and smooth spreadability on the human skin with some increase in stickiness. When the amount thereof is too large, on the other hand, the relative content of the thickening agent is consequently decreased so that no pasty consistency can be obtained.

The component (B) in the inventive composition is an oleaginous material selected from the group consisting of esters of a saturated fatty acid having 8 to 20 carbon atoms in a molecule and a saturated aliphatic alcohol having 1 to 20 carbon atoms in a molecule, animal oils, vegetable oils, squalane and petrolatum. These oleaginous materials can be used either singly or as a combination of two kinds or more according to need.

Examples of the esters of a saturated fatty acid having 8 to 20 carbon atoms in a molecule and a saturated aliphatic alcohol having 1 to 20 carbon atoms in a molecule include monoesters such as isopropyl myristate, butyl myristate, myristyl myristate, 2-octyldodecyl myristate, cetyl octanoate, butyl stearate, hexyl laurate, isopropyl palmitate, butyl palmitate and the like, diesters such as 1,3-bis(2-ethylhexanoyl)2,2-dimethyl propane and the like and triesters such as caprylic acid triglyceride, capric acid triglyceride and the like.

The animal and vegetable oils are exemplified by jojoba oil, soybean oil, peanut oil, wheat-germ oil, olive oil, rose oil, cottonseed oil, camellia oil, rubber seed oil, palm oil, macadamia oil, beeswax, lanolin, whale oil, beef tallow, lard and the like available on the market. Commercial products of squalane and petrolatum are also satisfactory.

These oleaginous materials can be used either singly or as a combination of two kinds or more according to need as the component (B). The amount of the component (B) in the inventive composition is in the range from 5 to 50% by weight or, preferably, from 7 to 45% by weight. When the amount thereof is too small, the component (C) described below can no longer be dissolved in the component (A) not to give a uniform mixture or not to impart a pasty consistency to the mixture. When the amount of the component (B) is too large, on the other hand, the pasty composition cannot exhibit light and smooth spreadability on the human skin with increased stickiness.

The component (C) in the inventive composition is a specific cellulose ether having ester-forming substituent groups derived from a saturated aliphatic carboxylic acid having 10 to 20 carbon atoms in a molecule. Such a cellulose derivative can be prepared by esterifying an alkyl cellulose, hydroxyalkyl cellulose or hydroxyalkyl alkyl cellulose by a conventional method of esterification using an acid anhydride or an acid chloride as the esterifying agent according to the procedure disclosed in, for example, U.S. Pat. Nos. 3,824,085 and No. 3,940,384. Examples of the alkyl cellulose include methyl cellulose, ethyl cellulose and the like. Examples of the hydroxyalkyl cellulose include hydroxyethyl cellulose, hydroxypropyl cellulose, hydroxybutyl cellulose and the like. Examples of the hydroxyalkyl alkyl cellulose include hydroxyethyl methyl cellulose, hydroxyethyl ethyl cellulose, hydroxypropyl methyl cellulose, hydroxypropyl ethyl cellulose, hydroxybutyl methyl cellulose and the like. The esterifying group should have 10 to 20 carbon atoms since a cellulose ether substituted with lower ester-forming groups has poor solubility in the component (A) so that no uniform composition can be obtained. Suitable ester-forming groups include those derived from a straightly linear alkyl group such as n-decanoyl, lauroyl, myristoyl, palmitoyl and stearoyl groups and those derived from a branched alkyl group such as isomyristoyl, isopalmitoyl and isostearoyl groups. The degree of substitution of the cellulose ether with these ester-forming groups should be such that the cellulose derivative contains at least 0.3 mole of the ester-forming groups per mole of the glucose units in the cellulose moiety. When the degree of substitution is too low, the cellulose derivative is poorly soluble in the component (A) so that no uniform pasty composition can be obtained. The amount of the cellulose derivative as the component (C) in the inventive composition is in the range from 2 to 30% by weight or, preferably, from 5 to 25% by weight. When the amount thereof is too small, the composition has no satisfactory pasty consistency. When the amount thereof is too large, on the other hand, the consistency of the composition is too high with decreased spreadability on the human skin.

The pasty composition of the present invention can be prepared by blending the above described components (A), (B) and (C) each in a calculated and weighed amount and agitating the mixture at an elevated temperature followed by cooling. The mixture is converted into a uniform mixture when it is heated and agitated at a temperature of 70° to 130° C. and the uniform mixture can be cooled without phase separation to give a highly viscous fluid or a pasty material having good spreadability. It is of course optional according to need that the inventive organopolysiloxane composition is further admixed with various kinds of known additives such as oiliness improvers, pigments, dyes, perfumes, antioxidants and the like.

The thus prepared pasty organopolysiloxane composition is particularly useful as a base for cosmetic and medicinal preparations by compounding with cosmetically or pharmacologically effective ingredients because the pasty composition exhibits good spreadability of the human skin and is capable of giving refreshingness to the user or patient as a consequence of the formulation with the cyclic organopolysiloxane as the principal ingredient having an adequately low viscosity and volatilizability not to give lasting feeling of wetness and stickiness.

In the following, the pasty organopolysiloxane composition of the invention is described in more detail by way of examples as preceded by the Synthetic Example for the preparation of the specific cellulose derivatives used in the compounding works of the inventive compositions. In the Examples, the values of the consistency of the compositions were calculated from the values of the ¼-consistency at 25° C. obtained by the measurements according to the procedure specified in JIS K 2220. The values of viscosity in the Examples are all those obtained by the measurement at 25° C. by use of a Brookfield-type rotation viscometer. The values of percentage are all in "% by weight".

SYNTHETIC EXAMPLE

Three kinds of cellulose ethers were used as the starting cellulose derivative including hydroxypropyl cellulose, hydroxyethyl ethyl cellulose and ethyl cellulose, hereinbelow referred to as the HPC, HEEC and EC, respectively, characterized as follows.

HPC: degree of substitution with hydroxypropoxy groups of 64%; viscosity of a 2% aqueous solution of 18,000 centistokes at 20° C.

HEEC: degree of substitution with hydroxyethoxy groups of 41%; degree of substitution with ethoxy groups of 15%; viscosity of a 2% aqueous solution of 13,000 centistokes at 20° C.

EC: degree of substitution with ethoxy groups of 45%; viscosity of a 5% solution in 8:2 mixture of toluene and ethyl alcohol of 70 centistokes at 25° C.

Into a glass flask of 1 liter capacity were introduced 10 g of one of the above characterized cellulose ethers together with pyridine or a combination of pyridine and toluene each in an amount indicated in Table 1 below and the mixture was heated at about 100° C. to dissolve the cellulose ether in the solvent. Thereafter, the esterifying agent or a mixture of two esterifying agents of the kind and in an amount each indicated in Table 1 was added dropwise into the solution kept at 90° to 100° C. over a period of 20 minutes and the reaction mixture thus formed was agitated for 6 hours at the above mentioned reaction temperature to effect the esterification reaction except that the temperature and reaction time were 110° to 120° C. and 3 hours in the esterification of HPC with acetic anhydride. After completion of the reaction and cooling to room temperature, the reaction mixture was poured into a large volume of water (HPC-Ac, see below) or methyl alcohol (other cellulose derivatives) under agitation to precipitate the esterified cellulose ether as the product. The precipitates were collected by filtration and thoroughly washed with methyl alcohol followed by drying to give the esterified cellulose ethers as desired. The products obtained in Preparations No. 1 to No. 5 shown in Table 1 were hydroxypropyl cellulose stearate laurate, hydroxypropyl cellulose laurate, hydroxyethyl ethyl cellulose laurate, ethyl cellulose laurate and hydroxypropyl cellulose acetate, referred to as the HPC-St-La, HPC-La, HEEC-La, EC-La and HPC-Ac, respectively, hereinbelow.

TABLE 1

| Preparation No. | Starting cellulose ether | Solvent(s) (amount taken, g) | Esterifying agent(s) (amount taken, g) |
|---|---|---|---|
| 1 | HPC | Pyridine (70) | Stearoyl chloride (54) |

TABLE 1-continued

| Preparation No. | Starting cellulose ether | Solvent(s) (amount taken, g) | Esterifying agent(s) (amount taken, g) |
|---|---|---|---|
|   |   | Toluene (500) | Lauroyl chloride (17) |
| 2 | HPC | Pyridine (70) Toluene (500) | Lauroyl chloride (77) |
| 3 | HEEC | Pyridine (58) Toluene (500) | Lauroyl chloride (46) |
| 4 | EC | Pyridine (13) Toluene (500) | Lauroyl chloride (28) |
| 5 | HPC | Pyridine (300) | Acetic anhydride (23) |

EXAMPLES 1 to 9 and COMPARATIVE EXAMPLES 1 and 2.

As the component (A) of each of the compositions prepared in Examples 1 to 9, decamethyl cyclopentasiloxane, referred to as $D_5$ hereinbelow, octamethyl cyclotetrasiloxane, referred to as $D_4$ hereinbelow, or a combination thereof was taken and admixed with an oleaginous material as the component (B) and the esterified cellulose ether prepared above as the component (C) as shown below in a proportion given in % in the same table. The mixture in a glass flask was heated at 120° to 130° C. under agitation in a stream of nitrogen gas by dipping the flask in an oil bath followed by continued agitation at the same temperature for 2 hours to give a uniformly compounded mixture. After cooling to room temperature, each of the thus prepared mixtures was a highly viscous liquid or had a pasty consistency without phase separation. Table 2 shows the consistency of the composition, when it had a pasty consistency, as unworked or as worked or the viscosity in centipoise of the composition, when it was liquid.

Oleaginous material [component (B)]
I: cetyl octanoate
II: squalane
III: jojoba oil
IV: soybean oil
V: isopropyl myristate
VI: petrolatum Each of the thus prepared highly viscous or pasty mixtures was tested organoleptically for the spreadability on the skin of several subject members of testing with a finger tip to find that each of the mixtures could be spread quite smoothly without giving unpleasant feeling of stickiness to the members who felt refreshingness by the application of these mixtures to their skin.

For comparison, a mixture of 85% of $D_5$ and 15% of HPC-St-La was prepared in Comparative Example 1 in substantially the same manner as above. The mixture was a cloudy liquid when it was hot but, upon cooling to room temperature, phase separation took place therein with appearance of precipitates due to poor compatibility of the cellulose derivative with the cyclic organopolysiloxane. For further comparison in Comparative Example 2, a mixture composed of 70% of $D_5$, 15% of jojoba oil and 15% of HPC-Ac was prepared but no clear and uniform mixture could be obtained even after prolonged agitation of the mixture at 120° to 130° C.

TABLE 2

| Example No. | Component (A) (%) | Component (B) (%) | Component (C) (%) | Consistency, unworked | Consistency, worked | Viscosity, cps |
|---|---|---|---|---|---|---|
| 1 | $D_5$(70) | I(17) | HPC—St—La | 320 | 370 | — |

TABLE 2-continued

| Example No. | Component (A) (%) | Component (B) (%) | Component (C) (%) | Consistency, unworked | Consistency, worked | Viscosity, cps |
|---|---|---|---|---|---|---|
| 2 | D$_5$(75) | II(10) | HPC—St—La (15) | 290 | 300 | — |
| 3 | D$_5$(80) | III(7) | HPC—La (13) | 360 | 350 | — |
| 4 | D$_5$(55) | I(20) | HPC—La (25) | 210 | 230 | — |
| 5 | D$_5$(15) D$_4$(60) | II(18) | HPC—La (7) | — | — | 690 |
| 6 | D$_5$(13) D$_4$(54) | IV(20) | HPC—St—La (13) | 320 | 340 | — |
| 7 | D$_5$(45) | V(45) | HEEC—La (10) | 380 | 420 | — |
| 8 | D$_5$(85) | VI(10) | HEEC—La (5) | — | — | 450 |
| 9 | D$_5$(50) | III(35) | EC—La (15) | 310 | 320 | — |

What is claimed is;

1. An organopolysiloxane composition which comprises, in admixture:
 (A) from 90 to 30% by weight of a cyclic organopolysiloxane represented by the general formula

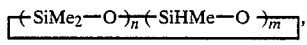

in which Me is a methyl group and m and n are each zero or a positive integer not exceeding 8 with the proviso that m+n is a positive integer of 3 to 8;
 (B) from 5 to 50% by weight of an oleaginous material selected from the group consisting of esters of a saturated fatty acid having 8 to 20 carbon atoms in a molecule and a saturated aliphatic alcohol having 1 to 20 carbon atoms in a molecule, animal oils, vegetable oils, squalane and petrolatum; and
 (C) from 2 to 30% by weight of a cellulose ether having ester-forming substituent groups derived from a saturated fatty acid having 10 to 20 carbon atoms in a molecule,
the total amount of the components (A), (B) and (C) being taken as 100% by weight.

2. The organopolysiloxane composition as claimed in claim 1 wherein the cyclic organopolysiloxane as the component (A) is selected from the group consisting of hexamethyl cyclotrisiloxane, octamethyl cyclotetrasiloxane, decamethyl cyclopentasiloxane, dodecamethyl cyclohexasiloxane, tetradecamethyl cycloheptasiloxane, hexadecamethyl cyclooctasiloxane, tetramethyl cyclotetrasiloxane, pentamethyl cyclopentasiloxane, pentamethyl cyclotetrasiloxane, hexamethyl cyclotetrasiloxane, heptamethyl cyclotetrasiloxane, hexamethyl cyclopentasiloxane, octamethyl cyclopentasiloxane, heptamethyl cyclopentasiloxane and nonamethyl cyclopentasiloxane.

3. The organopolysiloxane composition as claimed in claim 1 wherein the ester of a saturated fatty acid having 8 to 20 carbon atoms in a molecule and a saturated aliphatic alcohol having 1 to 20 carbon atoms in a molecule as the component (B) is selected from the group consisting of isopropyl myristate, butyl myristate, myristyl myristate, 2-octyldodecyl myristate, cetyl octanoate, butyl stearate, hexyl laurate, isopropyl palmitate, butyl palmitate, 1,3-bis(2-ethylhexanoyl) 2,2-dimethyl propane, caprylic acid triglyceride and capric acid triglyceride.

4. The organopolysiloxane composition as claimed in claim 1 wherein the animal oil as the component (B) is selected from the group consisting of beeswax, lanolin, whale oil, beef tallow and lard.

5. The organopolysiloxane composition as claimed in claim 1 wherein the vegetable oil as the component (B) is selected from the group consisting of jojoba oil, soybean oil, peanut oil, wheatgerm oil, olive oil, rose oil, cotton-seed oil, camellia oil, rubber seed oil, palm oil and macadamia oil.

6. The organopolysiloxane composition as claimed in claim 1 wherein the cellulose ether as the component (C) is selected from the group consisting of alkyl celluloses, hydroxyalkyl celluloses and hydroxyalkyl alkyl celluloses.

7. The organopolysiloxane composition as claimed in claim 1 wherein the ester-forming group of the cellulose ether as the component (C) is selected from the group consisting of n-decanoyl, lauroyl, myristoyl, palmitoyl, stearoyl, isomyristoyl, isopalmitoyl and isostearoyl groups.

8. The organopolysiloxane composition as claimed in claim 1 wherein the degree of substitution of the ester-forming groups on the cellulose ether as the component (C) is at least 0.3 mole of the ester-forming groups per mole of the glucose units in the cellulose moiety.

9. The organopolysiloxane composition as claimed in claim 2 wherein the cyclic organopolysiloxane as the component (A) is octamethyl cyclotetrasiloxane, decamethyl cyclopentasiloxane or a mixture thereof.

* * * * *